(12) United States Patent
Hedmann et al.

(10) Patent No.: US 9,907,898 B2
(45) Date of Patent: Mar. 6, 2018

(54) METHOD FOR CHECKING AND/OR MONITORING THE LEAK TIGHTNESS OF A PLURALITY OF PNEUMATICALLY OR HYDRAULICALLY ACTUATED ACTUATORS AND MACHINE, IN PARTICULAR MEDICAL TREATMENT MACHINE

(71) Applicant: Fresenius Medical Care Deutschland GmbH, Bad Homburg (DE)

(72) Inventors: Frank L. Hedmann, Volkach (DE); Stephan Klatte, Nienburg (DE)

(73) Assignee: FRESENIUS MEDICAL CARE DEUTSCHALND GMBH, Bad Homburg (DE)

( * ) Notice: Subject to any disclaimer, the term of this patent is extended or adjusted under 35 U.S.C. 154(b) by 421 days.

(21) Appl. No.: 14/585,414

(22) Filed: Dec. 30, 2014

(65) Prior Publication Data

US 2015/0141909 A1    May 21, 2015

Related U.S. Application Data

(63) Continuation of application No. 12/735,892, filed as application No. PCT/EP2009/001434 on Feb. 27, 2009, now Pat. No. 8,950,241.

(30) Foreign Application Priority Data

Feb. 29, 2008    (DE) .................. 10 2008 011 822

(51) Int. Cl.
*A61M 1/28* (2006.01)
*G01M 3/04* (2006.01)
*A61M 1/16* (2006.01)

(52) U.S. Cl.
CPC ................ *A61M 1/28* (2013.01); *G01M 3/04* (2013.01); *A61M 1/16* (2013.01);
(Continued)

(58) Field of Classification Search
CPC ...... A61M 1/16; A61M 1/28; A61M 2205/15; A61M 2205/52; A61M 2205/128; G01M 3/04

See application file for complete search history.

(56) References Cited

U.S. PATENT DOCUMENTS

| 5,431,626 A | 7/1995 | Bryant et al. |
| 5,634,896 A | 6/1997 | Bryant et al. |

(Continued)

FOREIGN PATENT DOCUMENTS

| DE | 10201109 | 1/2003 |
| DE | 112005000341 | 4/2007 |

(Continued)

*Primary Examiner* — Daniel S Larkin
(74) *Attorney, Agent, or Firm* — Jacobson Holman, PLLC.

(57) ABSTRACT

A method is provided of monitoring the leak tightness of a plurality of pneumatically or hydraulically actuated actuators of a machine, in particular a plurality of valve actuators of a medical treatment machine, in which pressure is exerted on the actuators in different combinations during operation of the machine. A common pressure drop occurring during a stationary operating phase at the actuators on which pressure is exerted in the respective combination is measured for a plurality of different combinations of actuators on which pressure is exerted. A respective leak tightness value is determined for individual actuators and/or groups of actuators, with the pressure drop measured for those combinations and in which the respective actuator and/or the respective group of actuators on which pressure is exerted being accounted for in the leak tightness value. A machine, in particular a medical treatment machine, is configured to effect the valve actuator monitoring.

42 Claims, 3 Drawing Sheets

(52) U.S. Cl.
CPC ... *A61M 2205/128* (2013.01); *A61M 2205/15* (2013.01); *A61M 2205/52* (2013.01)

(56) References Cited

U.S. PATENT DOCUMENTS

| | | |
|---|---|---|
| 6,804,991 B2 | 10/2004 | Balschat et al. |
| 2003/0061864 A1 | 4/2003 | Wong et al. |
| 2005/0126998 A1* | 6/2005 | Childers ............... A61M 1/28 210/646 |
| 2006/0195064 A1 | 8/2006 | Plahey et al. |
| 2007/0112297 A1 | 5/2007 | Plahey et al. |
| 2008/0236243 A1 | 10/2008 | Ciolkosz et al. |

FOREIGN PATENT DOCUMENTS

| | | |
|---|---|---|
| EP | 0293592 | 12/1988 |
| EP | 0856321 | 8/1998 |
| WO | WO 2005/091924 | 10/2005 |

\* cited by examiner

METHOD FOR CHECKING AND/OR MONITORING THE LEAK TIGHTNESS OF A PLURALITY OF PNEUMATICALLY OR HYDRAULICALLY ACTUATED ACTUATORS AND MACHINE, IN PARTICULAR MEDICAL TREATMENT MACHINE

CROSS-REFERENCE TO RELATED APPLICATION

This application is a continuation application of U.S. application Ser. No. 12/735,892 filed Aug. 24, 2010, now issued by the U.S. Patent and Trademark Office as U.S. Pat. No. 8,950,241, the disclosure of which is incorporated by reference as is fully set forth herein. The predecessor application, U.S. application Ser. No. 12/735,892, is a nationalization of PCT/EP09/001434 filed Feb. 27, 2009, and published in German.

BACKGROUND OF THE INVENTION

1. Field of Invention

The present invention relates to a method for checking and/or monitoring the leak tightness of a plurality of pneumatically or hydraulically actuated actuators of a machine, in particular a plurality of valve actuators of a medical treatment machine, as well as to a machine, in particular a medical treatment machine, having a control for the carrying out of the corresponding methods.

The present invention in particular relates to a method for checking and/or monitoring the leak tightness of a plurality of pneumatically or hydraulically actuated actuators of a machine in which a cassette system is used for the transport of liquids, in particular medical liquids. The method in accordance with the invention can be used particularly advantageously in the area of dialysis, in particular of peritoneal dialysis, in particular in treatment machines having a cassette system for the transport of the treatment liquids or for the carrying out of the treatment. The method can equally be used in hemodialysis or in infusion systems.

2. Description of the Prior Art

The present invention in particular relates to peritoneal dialysis machines such as are presented in US 2007/0112297 A1 and US 2006/0195064 A as well as to methods for the operation of such peritoneal dialysis machines. The full extent of the content of 2007/0112297 A1 and US 2006/0195064 A1 is hereby an integral part of the disclosure of the present application.

The pneumatically or hydraulically actuable actuators of the machine are advantageously valve actuators with which the valves used in these cassette systems are switched. The cassettes are made as disposable articles and have valve points on which the valve actuators of the machine act and thus switch the valves. The cassettes in particular have liquid conducting passages which have at least one flexible wall in the region of the valve points which can be pressed into the liquid conducting passage by the valve actuator and thus block said passage. In this connection, the actuators advantageously have a flexible region which expands when pressure is exerted on the actuator and thus acts as a valve tappet. Hydraulically or pneumatically actuable pistons can equally be used as actuators which advantageously likewise serve as valve tappets. In such cassette systems, the region advantageously at the cassette side for the conveying of the process liquid such as the dialysate is separated by at least one membrane from the region advantageously at the machine side on which pressure is exerted for the actuation of the actuators.

During ongoing operation of the machine, different switching patterns of the valves are run through to provide the liquid paths required in the cassette e.g. during a purging process or during a treatment. The actuators of the machine have pressured exerted on them for this purpose during the ongoing operation of the machine in different combinations in order thus to switch the corresponding valves in the cassette accordingly and to provide the desired fluid paths for the operation of the cassette.

The actuators usually have an active switching state in which pressure is exerted on them and an inactive switching state in which pressure is not exerted on them. It is possible to switch to and fro between these states by exerting pressure on the actuators or removing the pressure. During such switching processes, the pressure applied to the system changes, whereas a stationary state is adopted between the switchover processes in which the pressure applied to the actuators on which pressure is exerted being substantially constant. However, with pneumatically or hydraulically actuable actuators leaks can occur on the side on which pressure is exerted.

In known methods for checking and/or monitoring the leak tightness of such actuators, an initial test is therefore usually carried out at the start of the treatment in which test pressure is exerted on the actuators and the pressure drop per time unit is measured in the subsequent stationary state to determine any leaks. If the pressure drop per time unit exceeds a certain limit value in this connection, the operation of the device is not released.

A leak present on the initialization of the device can admittedly be recognized with such a method. However, there is no longer any possibility to determine whether a leak has arisen in the system during the operation of the device. In particular no initial test can be carried out during the operation of the machine since the machine would have to be stopped completely for this purpose. Furthermore, there is no indication of when a suitable time for such a test during the treatment would be. Leaks in the actuators can, however, particularly arise during the ongoing treatment due to wear of the actuators.

SUMMARY OF THE INVENTION

It is therefore the object of the present invention to provide a method for checking and/or monitoring the leak tightness of a plurality of pneumatically or hydraulically actuated actuators which can be carried out during the ongoing operation of the machine. It is furthermore the object of the present invention to provide a machine, in particular a medical treatment machine, having corresponding valve actuator monitoring.

This object is solved is accordance with the invention by a method and a machine as described herein. Advantageous aspects of the aforementioned embodiments of the invention are also described herein.

In this connection, the invention includes a method for checking and/or monitoring the leak tightness of a plurality of pneumatically or hydraulically actuated actuators of a machine, in particular of a plurality of valve actuators of a medical treatment machine, with pressure being exerted on the actuators in different combinations during operation. In accordance with the invention, the pressure drop occurring during a stationary operating phase at the actuators on which pressure is exerted in the respective combination is measured together for a plurality of different combinations of actuators on which pressure is exerted. For individual actuators and/or individual groups of actuators, a leak tightness value is then respectively determined into which a pressure drop is taken which is measured for those combinations in which pressure is exerted on the respective actuator and/or the respective group of actuators.

The machine in accordance with the invention exerts pressure on the actuators in different combinations during its operation to switch the valves on the cassette side and thus to establish the desired liquid paths. Switching operating phases hereby result in which switching takes place between different combinations of actuators on which pressure is exerted so that the system pressure fluctuates and stationary operating phases which are disposed therebetween and in which a substantially constant system pressure is applied to a fixed combination of actuators which is not changed by switchover processes and which can only reduce over time due to the leak of the system. The pressure drop in these stationary operating phases is therefore a measure for the leak tightness of the actuators on which pressure is just being exerted.

During these stationary operating phases, the pressure now respectively applied at all actuators together on which pressure is exerted is measured and the pressure drop is measured which arises during these stationary operating phases. The pressure drop is advantageously measured for the time period in which there is a corresponding combination. The pressure applied at all actuators together on which pressure is exerted can in particular be measured at two different points in time during the stationary operating phase, in particular at the start and at the end of the stationary operating phase and the pressure drop can be determined from the difference of the two values. On a switchover process, the pressure drop measured is then advantageously supplied to an evaluation unit and is advantageously stored in a table.

An individual measurement of the pressure drop for only a combination of actuators on which pressure is exerted usually does not allow any reliable conclusions on the leak tightness of individual actuators and/or individual groups of actuators since a plurality of actuators usually have pressure exerted on them simultaneously in such a combination and the measured pressure drop thus forms a collective value for the sum of all leaks of the participating actuators.

Now, however, a leak value for individual actuators and/or individual groups of actuators can also be determined from the data for a plurality of different combinations of actuators on which pressure is exerted. In this connection, the pressure drop measured for a specific combination is taken into the leak tightness value of a specific actuator if this actuator had pressure exerted on it in this combination. If, in contrast, an actuator did not have pressure exerted on it in a specific combination, the pressure drop measured during this combination is not taken into the leak value of this actuator.

A trend for an actuator or for a group of actuators can thus be determined from the values collected thereby, at least after a specific time or frequency of the measurements. Although usually pressure is exerted on a plurality of actuators simultaneously during the usual ongoing operation of the machine, the leak tightness of every individual actuator can thus be evaluated by the collection of values from a plurality of different combinations. In accordance with the invention, the fact is utilized in this connection that pressure is anyway exerted on a plurality of different combinations of actuators in the operation of the machine. An estimate of the leak tightness of the individual actuators can thus be gained by evaluation of the pressure drop for these different combinations.

The respective measurement time during which the pressure drop occurred is advantageously taken into the leak tightness value in addition to the pressure drop. In the method in accordance with the invention, in addition to the pressure drop occurring for the respective combination, the measuring time during which this pressure drop occurred can accordingly also be taken into account. For this purpose, the pressure drop and the measuring time are advantageously transmitted to an evaluation unit for the respective stationary operating phase. Since the pressure drop occurring during a stationary operating phase also depends on the measuring time in addition to the leak of the respective actuators on which pressure is exerted, a more precise detection of leaks is possible by the taking into account of these measuring times.

In this connection, a pressure drop per time unit formed from the common pressure drop values and the measuring times can in particular be taken into the leak tightness value. The pressure drop per time unit forms a relatively precise measure for the leak tightness of the respective actuators in this connection.

Advantageously, for the determination of the leak tightness value of an individual actuator and/or of an individual group of actuators, a mean value is formed into which the pressure drop and advantageously the measuring time for all those combinations of actuators on which pressure is exerted are taken in which pressure was exerted on the respective actuator and/or the respective group of actuators. A mean value is therefore formed for the determination of the leak tightness value of a specific actuator from all those measured values for the pressure drop which were measured in operating phases in which pressure was exerted on this specific actuator. Although every single actuator has, as the case may be, only caused a specific portion of the pressure drop itself in these operating phases, whereas another portion of the pressure drop was caused by further actuators on which pressure was likewise exerted, a value for the leak tightness results for every single actuator in a relatively good approximation by this averaging over a plurality of different combinations of actuators. In this connection, the measuring times for the respective pressure drop are also respectively taken into the mean value formation, with a mean value of the measured pressure drop per time unit in particular being able to be formed.

In this connection, for the determination of the leak tightness value of an individual actuator and/or of an individual group of actuators, the optionally weighted mean value of the pressure drop and/or of the pressure drop per time unit of all those combinations of actuators on which pressure is exerted is/are advantageously calculated in which pressure is exerted on the respective actuator or the respective group of actuators.

The optionally weighted mean value formation can take place in different manners. In this connection, in particular all the combinations in which pressure was exerted on an actuator can be weighted equally so that the pressure drop and/or the pressure drop per time unit measured for a specific combination is taken into the mean value formation for the leak value of the participating actuators independently of the duration and of the number of the actuators on which pressure is exerted.

However, advantageously, the duration of the stationary operating phases in which the pressure drop and/or the pressure drop per time unit was measured is taken into the mean value formation. In this connection, in particular the time mean value of the pressure drop per time unit measured during all the stationary operating phases in which pressure was exerted on this actuator can be formed for the leak tightness value of a specific actuator. Combinations which are present over a longer period are hereby weighted more than combinations which are only switched for a brief time. With combinations with longer stationary operating phases, however, the measured values for the pressure drop per time unit are also more precise so that the precision hereby increases.

In this connection, for the determination of the leak tightness value of an individual actuator and/or of an individual group of actuators, the sum of the pressure drops and the sum of the measuring times for all those combinations of actuators on which pressure is exerted are advantageously determined at which pressure is exerted on the respective actuator and/or on the respective group of actuators. A mean pressure drop per time unit can then be determined from the quotient of these two sums which is taken into the leak tightness value of the actuator and/or of the group of actuators.

Furthermore, the number of the actuators on which pressure is exerted in a specific combination can advantageously be taken into the mean value formation. In this connection, the pressure drop determined for a specific combination can in particular be taken the less into the leak tightness values of the participating actuators, the more actuators had pressure exerted on them. It is hereby prevented that combinations with a large number of actuators on which pressure is exerted and in which correspondingly high common pressure losses occur are included over proportionally in the mean value formation.

Alternatively, however, provision can also be made that the common pressure drop measured for a specific combination of actuators on which pressure is exerted is taken into the mean value formation independently of the number of the actuators on which pressure is exerted in this combination. The leak tightness values associated with an actuator with a high leak rate is hereby not reduced in that this actuator is operated together in combination with other actuators which have a substantially lower leak rate. Accordingly, defective actuators can be recognized particularly easily by such a combination, but also the values of the actually correctly working actuators.

Further advantageously, in accordance with the invention, the common pressure drop for all actuators on which pressure is exerted in the respective combination and measured for a specific combination of actuators on which pressure is exerted is taken into the leak tightness value of said actuators in equal amounts. Such a uniform distribution of the values is in particular meaningful when all actuators have an identical structure.

Further advantageously, in accordance with the invention, the leak tightness values of the individual actuators and/or of individual groups of actuators are updated continuously during the operation of the machine. The leak tightness values of the individual actuators and/or of individual groups of actuators are in particular advantageously updated when the machine switches over from one combination of actuators on which pressure is exerted into another combination. The pressure drop or the pressure drop per time unit measured during the stationary operating phase of the previous combination is then advantageously used for the updating of the leak tightness values of the individual actuators and/or of the individual groups of actuators, whereas a new pressure measurement is started on the reaching of the stationary operating phase of the new combination.

For the checking and/or monitoring of the actuators, the range of the specific leak tightness values is advantageously used in the method in accordance with the invention. In this connection, the lowest leak tightness value is compared with the highest leak tightness value and thus the range of the leak tightness values over all actuators is determined. A low range is an indicator for a high leak tightness of the actuators, whereas a high range is an indicator for a leak since evidently at least one actuator is present which has a substantially different leak tightness value than the remaining actuators.

Further advantageously, the sum of all the determined leak tightness values is used for the checking and/or monitoring of the actuators. This sum also permits a global statement on the leak tightness of the system.

Further advantageously, the change over time of the determined leak tightness values is used for the checking and/or monitoring of the actuators. It can hereby be determined whether pronounced changes in the leak tightness occur with individual actuators or individual groups of actuators.

A leak can thus be recognized during the ongoing operation of the machine by evaluating the corresponding leak tightness values. The ongoing operation is advantageously stopped and a test carried out on a recognition of a leak. It can now again be ensured by such a test that the values determined during the ongoing operation do not represent an incorrect measurement, but that a leak is actually present.

In this connection, an initial test can be carried out as the test in which all the actuators are checked. Such an initial test routine is already provided with known devices and is initially carried out before the putting into operation.

Alternatively, a test can also be carried out in which only the individual actuator and/or the individual group of actuators is checked in which a leak was recognized. A fast check of the leak determined during the ongoing operation is hereby possible. If the leak is not confirmed in the individual actuator or in the individual group of actuators, an initial test can still be carried out as required to check whether a leak is present in other actuators.

Further advantageously, on the recognition and/or confirmation of a leak, the leaking actuator is not further used or the machine is put into a secure state. Since a number of fluid paths can be provided in a cassette by switching different actuators, it is possible not to actuate individual actuators during the ongoing operation and nevertheless to continue to operate the machine. In accordance with the invention, actuators recognized as leaking can therefore be shut down without impairing the safety of the cassette. If this is not possible, the machine, in contrast, switches into a safe state until a repair has been made.

Generally, when a leak was recognized, safety measures can then be initiated. An alarm can in particular also be triggered in this connection.

Advantageously, the machine in accordance with the invention is used for the control of the valves of a cassette for the transport of a medical liquid, in particular in dialysis. Such cassettes usually have liquid conducting passages which have at least one flexible wall in the region of the valve points which is pressed into the passages to block them. The liquid conducting passages are in particular covered via a flexible membrane. By pressing this membrane into the liquid conducting passages, they can then be blocked so that valves are produced. The actuators in accordance with the invention advantageously work as valve tappets to press the flexible wall or membrane into the liquid conducting passages. An actuator in accordance with the invention can in particular have a flexible region which expands on the application of pressure and is thus pressed into the liquid conducting regions of the cassette.

The present invention furthermore includes a machine, in particular a medical treatment machine, having a plurality of pneumatically or hydraulically actuable actuators, in particular a plurality of valve actuators, and having a pressure measuring device for the measurement of the pressure applied together to the actuators on which pressure is exerted as well as having an electronic control for the carrying out, in particular the automatic carrying out, of a method such as was described above. The electronic control in accordance with the invention advantageously has a correspondingly designed computing unit as well as a memory for the storage of the leak tightness values. The same advantages obviously result from such a machine which were presented further above with respect to the method. The machine can in particular carry out the method in accordance with the invention for checking or monitoring the leak tightness of the actuators of the machine automatically during the ongoing operation of the machine so that the safety of operation is increased.

Advantageously, the machine is a machine for the control of the valves of a cassette for the transport of a medical liquid, and indeed in particular a machine for use in dialysis, in particular in peritoneal dialysis. The cassette is inserted into such a machine as a disposable element and serves the transport of a medical liquid, e.g. of the dialysate. The actuators in accordance with the invention are then coupled to the cassette and are used as valve actuators for the control of the valves of the cassette.

The present invention thus includes a machine, in particular a medical treatment machine, having a plurality of pneumatically or hydraulically actuable actuators, in particular a plurality of valve actuators, having a pressure measuring device for the measurement of the pressure applied to the actuators together on which pressure is exerted, and having an electronic control which controls the actuators and the pressure measuring device such that the actuators have pressure exerted on them in different combinations during the operation of the machine and the common pressure drop occurring during a stationary operating phase at the actuators on which pressure is exerted in the respective combination is measured for a plurality of different combinations of actuators on which pressure is exerted. The machine furthermore includes an evaluation unit which in each case determines a leak tightness value for individual actuators and/or individual groups of actuators, with the pressure drop measured for those combinations in which pressure is exerted on the respective actuator and/or the respective group of actuators being taken into said leak tightness value. Furthermore, a checking and/or monitoring unit is provided which checks and/or monitors the leak tightness of the actuators of the machine based on the leak tightness values determined. The machine in accordance with the invention also thus has the possibility of continuously monitoring the leak tightness of the pneumatically or hydraulically operated actuators during ongoing operation without the operation of the machine having to be interrupted for this purpose.

Advantageously, in addition to the pressure drop, the respective measuring time during which the pressure drop occurred is taken into the leak tightness values formed by the evaluation unit. Since the pressure drop which occurs during a stationary operating phase at the actuators on which pressure is exerted together in the respective combination is, in addition to the leaks of the actuators on which pressure is respectively exerted, also dependent on the measuring time during which the pressure drop is determined, a more precise determination of the leak tightness values thus results. The pressure can in particular be measured during two different times of a stationary operating phase and the pressure drop hereby determined can be transferred to the evaluation unit together with the time period between the two times. A memory can likewise be provided in which these values or values calculated therefrom are stored.

Advantageously, a pressure drop per time unit formed from the measured pressure drop values and from the measuring times is taken into the leak tightness value. The pressure drop per time unit is a relatively precise measure for the leak tightness of an actuator and/or an individual group of actuators. In this connection, both the respective pressure drop per time unit measured for the different combinations of actuators on which pressure is exerted can be taken into the evaluation and/or a mean pressure drop per time unit can be determined from the measured pressure drop values and the measuring times for a plurality of combinations.

Advantageously, the evaluation unit forms a mean value for the determination of the leak tightness value of an individual actuator and/or of an individual group of actuators and the pressure drop and advantageously the measuring time for all those combinations of actuators on which pressure is exerted is taken into said mean value at which pressure was exerted on the respective actuator and/or the respective group of actuators. A good approximation to the actual leak tightness value of the respective actuator or the respective group of actuators thus results from the mean value formation over the measured values for all the combinations in which pressure is exerted on a specific actuator or a specific group of actuators.

Advantageously, the evaluation unit calculates the leak tightness value of an individual actuator and/or of an individual group of actuators as the optionally weighted mean value of the pressure drop and/or of the pressure drop per time unit of all those combinations of actuators on which pressure is exerted in which pressure is exerted on the respective actuator and/or the respective group of actuators. The weighting of the measured values for the pressure drop and/or the pressure drop per time unit for the respective combination of actuators on which pressure is exerted can take place in different manners.

The duration of the stationary operating phases for which the pressure drop and/or the pressure drop per time unit was determined can in particular be taken into the mean value formation. In particular when a mean value of the measured pressure drops per time unit is formed, that is when the measuring times are anyway taken into the leak tightness values, the duration of the stationary operating phases or the measuring times can be taken into the mean value formation in addition thereto. The temporal mean value can in particular be formed.

Furthermore, the number of the actuators in which pressure is exerted in a specific combination can be taken into the mean value formation. Alternatively to this, the measured common pressure drop for a specific combination of actuators on which pressure is exerted can go into the mean value formation independently of the number of the actuators on which pressure is exerted in this combination. Leaking actuators are hereby easier to recognize, but also influence the leak tightness values of actually leak tight actuators more.

Advantageously, the common pressure drop for all the actuators on which pressure is exerted measured for a specific combination of actuators on which pressure is exerted is taken into account in the leak tightness value of said actuators in equal amounts. The reasons for this procedure are that the system has no more detailed information on how a common pressure drop of a plurality of actuators on which pressure is actuated is due to the individual actuators. Due to the use of measured values of a plurality of different combinations of actuators, a relatively good approximation to the actual leak tightness of the individual actuator or of the group of actuators nevertheless results over time for each individual actuator or for each specific group of actuators.

Advantageously, for the specific implementation of the method in accordance with the invention, the evaluation unit for the determination of the leak tightness values of an individual actuator and/or an individual group of actuators can determine the sum of the pressure drops and the sum of the measuring times for all those combinations of actuators on which pressure is exerted in which pressure was exerted on the respective actuator and/or the respective group of actuators. A mean pressure drop per time unit can then be formed for each actuator for each group of actuators from this sum of the pressure drops and this sum of measuring times and the leak tightness value of the respective actuator or the respective group of actuators in turns results from said mean pressure drop per time unit. Such a procedure corresponds to the formation of the temporal mean value over the pressure drop per time unit of all those combinations of actuators on which pressure is exerted and in which pressure is exerted on the respective actuator and/or the respective group of actuators.

Further advantageously, in accordance with the invention, the evaluation unit updates the leak tightness values of the individual actuators and/or individual groups of actuators continuously during the operation of the machine. A reliable checking and/or monitoring of the leak tightness of the actuators hereby results.

The checking and/or monitoring unit advantageously checks and/or monitors the leak tightness of the actuators on the basis of the range of the leak tightness values determined. A high range of leak tightness values is an indicator of a leaking actuator, whereas a low range is an indicator for the leak tightness of all actuators.

Further advantageously, the checking and/or monitoring unit checks and/or monitors the leak tightness of the actuators based on the sum of all leak tightness values determined. This sum of all determined leak tightness values is a value which corresponds to the total leak tightness of the system.

Further advantageously, the checking and/or monitoring units of the machine in accordance with the invention checks and/or monitors the leak tightness of the actuators based on the change over time of the leak tightness values determined. Such a change in the determined leak tightness values can be an indicator for the occurrence of such a leak.

Obviously, in this connection, a combination of a plurality of values can also be used for checking and/or monitoring the leak tightness of the actuators.

Further advantageously, the checking and/or monitoring unit stops the ongoing operation of the machine and carries out a test on the recognition of a leak. By this test, the leak tightness of a specific actuator or of a specific group of actuators determined during the ongoing operation can be checked or confirmed again e.g. by the checking and/or monitoring unit by this test.

In accordance with the invention, an initial test can be carried out in which all actuators are checked. Alternatively, however, a test can be carried out in which an individual actuator and/or an individual group of actuators are checked in which a leak was recognized. All the actuators no longer have to be checked since initially, for the confirmation of the leak, a check of the actuator or group of actuators is sufficient in which the checking and/or monitoring unit had recognized the leak.

Advantageously, the control of the machine in accordance with the invention no longer uses the leaking actuator on a recognition and/or confirmation of a leak. The control can in particular continue the operation of the machine if this is possible while bypassing the leaking actuator. Otherwise, the machine switches into a safe state.

Advantageously, the machine in accordance with the invention is used for the control of the valves of a cassette for the transport of a medical liquid, in particular for use in dialysis. In this connection, the cassette usually forms a disposable part which is inserted into the machine, with the machine controlling the liquid flows in the cassette.

Advantageously, the machine in accordance with the invention has a coupling surface to which a cassette for the transport of a medical liquid can be coupled, with the actuators being arranged at the coupling surface. The actuators at the machine side can thus engage onto the valves of the coupled cassette and thus provide different fluid paths in the cassette.

The present invention further advantageously includes a computer program product, in particular a storage medium with a computer program, in particular for transfer to a machine, with commands for the carrying out of a method such as was described above. The same advantages as were described with respect to the method also result from such a computer program product. Such a computer program stored on a storage medium can in particular be transferred to an existing machine to carry out the method in accordance with the invention there for checking and/or monitoring the leak tightness of the actuators of the machine. Existing machines can hereby be retrofitted with the method in accordance with the invention. This is in particular possible without problem in that no additional components are required to carry out the method.

BRIEF DESCRIPTION OF THE DRAWINGS

The present invention will now be described in more detail with reference to an embodiment and to the drawings. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The present invention will now be presented in more detail with reference to an embodiment in which the method in accordance with the invention for checking and/or monitoring the leak tightness of a plurality of pneumatically actuable valve actuators of a medical treatment machine is used.

Disposable cassettes are usually used in such medical treatment machines for the transport of medical liquids. These disposable cassettes have liquid passages which are covered by a flexible foil. The disposable cassette is inserted into the treatment machine in this connection and is coupled to a coupling surface at the device side such that the actuators arranged in the coupling surface of the treatment machine can press the flexible foil of the cassette into the liquid conducting passages and thus determine the fluid paths in the cassette. The pneumatically actuated actuators advantageously have flexible regions which expand on the application of pressure to the actuator and thus press the flexible foil into the liquid conducting passages. Pumps and the like can hereby also be realized in addition to valves.

Figure 5:
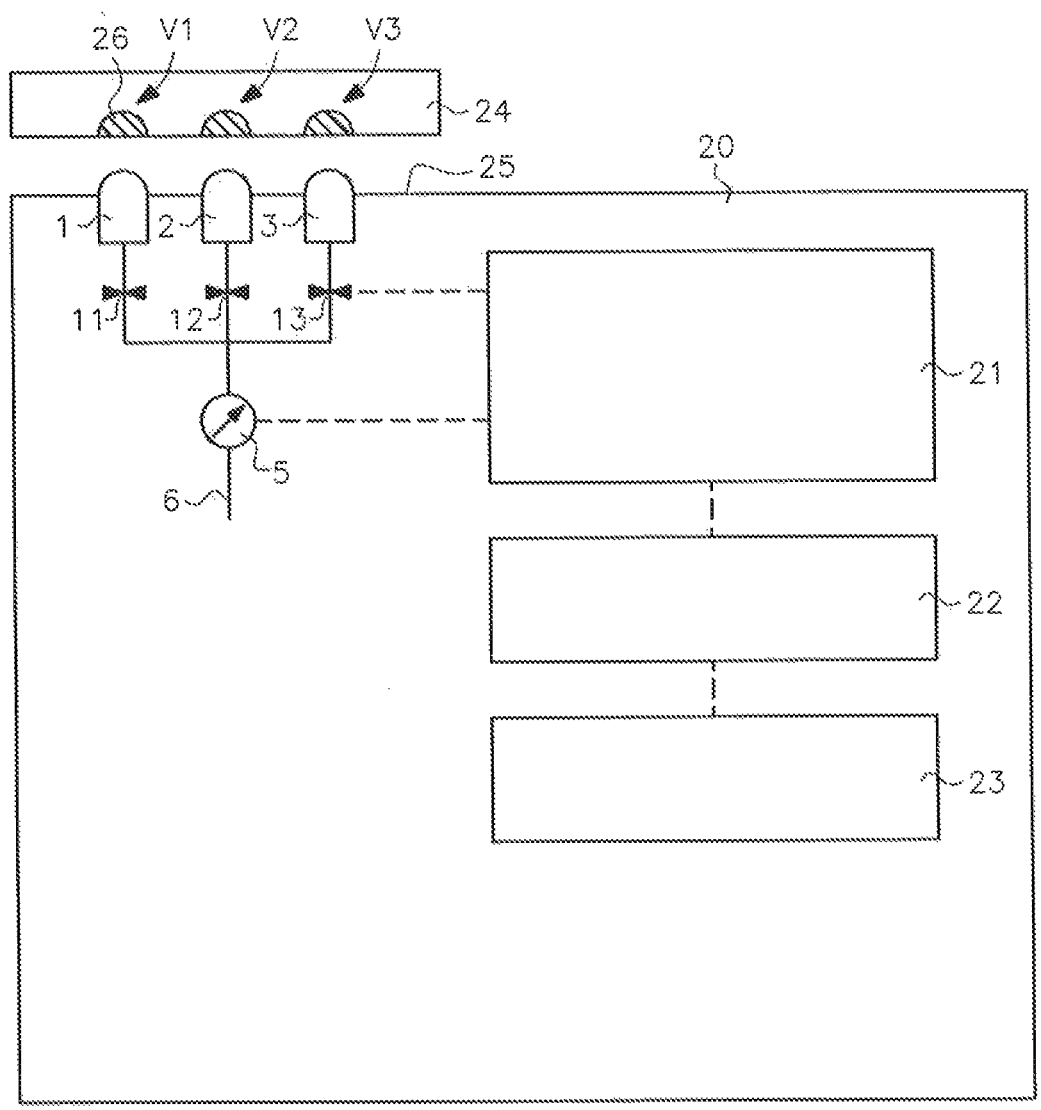
FIG. 5 illustrates a medical treatment machine in accordance with an embodiment of the present invention, and a cassette for the transport of a medical liquid.

FIG. 5 illustrates a medical treatment machine 20 in accordance with an embodiment of the present invention, and a cassette 24 for the transport of a medical liquid 26. The cassette 24 includes valves V1, V2, and V3. The medical treatment machine 20 includes valve actuators 1, 2, and 3, which cooperate with, respectively, valves V1, V2, and V3 of the cassette 24 via a coupling surface 25. Actuation of the valve actuators 1, 2, and 3 is effected via a central pressure supply 6 having a pressure gauge 5. The valve actuators 1, 2, and 3 are associated with, respectively, apparatuses 11, 12, and 13 for selectively exerting pressure on the valve actuators 1, 2, and 3 or isolating the valve actuators 1, 2, and 3 from the central pressure supply, respectively. Control of the valve actuators 1, 2, and 3 is effected with an electronic control unit 21, which is associated with an evaluation unit 22 and a monitoring unit 23.

In this connection, during the ongoing operation of the treatment machine, pressure is alternatively exerted on different combinations of actuators in order to establish correspondingly different fluid paths in the cassette. In this connection, typically pressure is exerted simultaneously on a plurality of valves in each combination so that the pressure loss which occurs on all valves together on which pressure is exerted during a specific combination cannot be associated with an individual valve. To check the leak tightness of the individual actuators of the treatment machine in accordance with the invention, the method in accordance with the invention is now used which is carried out during the normal operation of the treatment machine. It is possible with the method in accordance with the invention to associate a corresponding leak tightness value to every single actuator by the use of data from a plurality of different combinations of actuators on which pressure is exerted.

In this connection, the pressure drop which initially occurs during a stationary operating phase at the actuators on which pressure is exerted together in the respective combination for a plurality of different combinations of actuators on which pressure is exerted is measured and is stored together with the measuring time. A respective leak tightness value is now determined from these data for individual actuators and/or individual groups of actuators and the pressure drop or the pressure drop per time unit measured for those combinations in which pressure is exerted on the respective actuator and/or the respective group of actuators is taken into said lead tightness value.

The course of the operating pressure in the system can be divided into two phases: in a first phase, a changed pressure range occurs since a switch is made from a combination of valves on which pressure is exerted to another combination so that pressure accordingly has to be built up. Stationary phases occur between these switchover phases and no actions are carried out in them. A stable pressure which is now measured in accordance with the invention is present in these stationary operating phases. In this connection, the respective pressure drop for the different combinations is measured during the stationary operating phase associated with a specific combination and is transferred to an evaluation unit together with the measuring time. The pressure drop measured during such a stationary operating phase and the measuring time are then associated with all those actuators on which pressure was exerted during this specific combination. The leak tightness value associated with each actuator thus results in the course of the operation from the averaged pressure drop of the combinations in which the respective actuator participated.

In FIGS. 1 to 4, different combinations of actuators on which pressure is exerted are shown for illustration. In this connection, the actuators 1, 2, 3 are shown as representative for the usually considerably higher number of actuators (e.g. 16 actuators) in a treatment machine on which in each case pressure is exerted via apparatus 11, 12 and 13 or which can be cut off from the pressure supply. The apparatus 11, 12 and 13 are shown filled in in black in this connection when pressure is exerted on the associated actuators 1, 2 or 3 or are colored white when no pressure is exerted on the corresponding actuators. In this connection, a central pressure supply is provided for all the actuators on which pressure is exerted whose pressure can be determined using the pressure gage 5.

Figure 1:
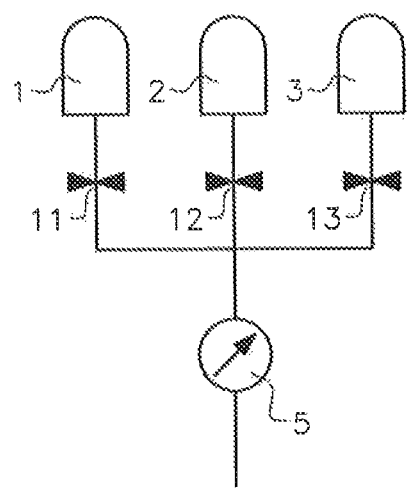
FIGS. 1-4: different combinations of actuators on which pressure is exerted during the operation of a machine in accordance with the invention.
Figure 2:
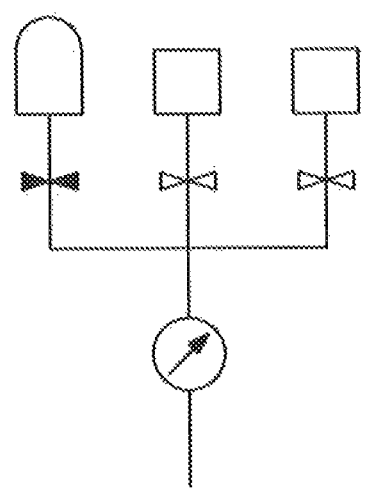
Figure 3:
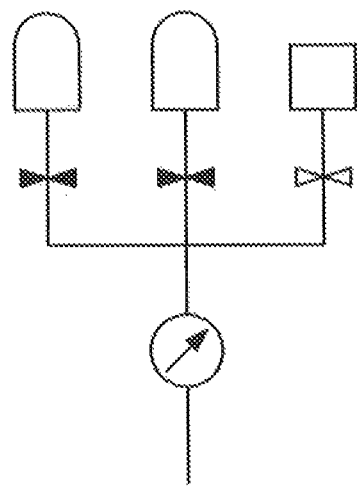
Figure 4:
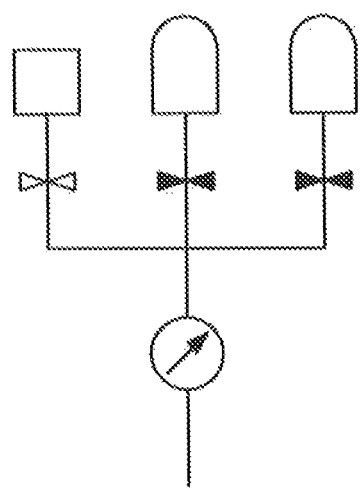

In FIG. 1, a first combination is shown in which pressure is exerted on all the actuators. In FIG. 2, in contrast, pressure is only exerted on actuator 1, whereas the actuators 2 and 3 are not active. In FIG. 3, pressure is exerted on the actuators 1 and 2, while the actuator 3 is not active. In FIG. 4, actuator 1 is not active, while pressure is exerted on actuators 2 and 3.

It is now shown in the form of a table how the leak rate of the individual actuators can be determined during the ongoing operation of the treatment machine by the measurement of the pressure drop and the association of the values to the actuators on which pressure is respectively exerted. A valve pattern in the cassette results in this connection by acting on different combinations of actuators.

A specific common leak rate of the active actuators then results for each combination from the respectively used combination of actuators on which pressure is exerted. The embodiment starts from a leak rate of the actuators 1 to 3 associated with the valves V1 to V3 of V1: 5 mbar/min
V2: 15 mbar/min
V3: 0 mbar/min In this connection, after a switching over of the actuator, it is first waited until a stationary operating state has been adopted. Thereupon, the pressure is measured in the embodiment for as long as the corresponding combination is present. On a change of the valve pattern with a correspondingly new combination of actuators on which pressure is exerted, the pressure drop measured for the preceding combination is supplied together with the measuring time to an evaluation unit and is e.g. stored in a table, with the measured values only being associated with those actuators on which pressure is exerted in the corresponding combination. Thereupon, the mean value of the measured values associated with the actuators is formed for all the actuators.

The leak tightness value associated with each actuator thus corresponds to the temporal mean value of the common pressure drop per time unit of all previous combinations in which pressure was exerted on the respective actuator.

In the pattern 1 shown in Table 1, which corresponds to an arrangement in accordance with FIG. 1, pressure is exerted on all the actuators and all the valves V1 to V3 are accordingly closed. A common leak rate of all actuators of 20 mbar/min hereby results. The pressure drop during the presence of pattern 1 is measured and is stored in the table, together with the then current measuring time for all participating actuators. A switch is thereupon made to pattern 2 which corresponds to FIG. 2 and in which pressure is only exerted on actuator 1. A leak rate of 5 mbar/min hereby results. The corresponding pressure drop and the measuring time are accordingly also only associated with actuator 1. With pattern 3, which corresponds to FIG. 3, pressure is then exerted on the first two actuators, whereby a common leak rate of 20 mbar/min results. The pressure drop which hereby arises is then stored in the table together with the measuring times for the participating actuators 1 and 2.

If now the total respective pressure drop associated with an actuator is divided by the total measuring time associated with an actuator, a mean pressure drop per time unit results for each actuator. The more combinations are taken into such a leak tightness value, the more closely the actual leak rate is approximated. In this connection, however, leaking valves can be recognized more clearly than leak tight valves since the result of the leak tight valves is influenced by the leaking valves.

This can be recognized in the evaluation e.g. in accordance with pattern 7 in which a leak rate of 10 mbar/min is associated with actuator 1, a leak rate of 16.7 mbar/min with actuator 2 and a leak rate of 5 mbar/min with actuator 3.

The method shown in the table for the determination of the leak tightness values of the individual actuators can be implemented particularly simply since the respectively measured pressure drop over the duration of the stationary operating phases is associated in the same way with all actuators on which pressure is exerted during this operating phase without the number of valves on which pressure is exerted being taken into account. The time average over all the operating phases in which pressure was exerted on the actuator then results as the average value for each actuator. It is hereby ensured that the mean leak rate determined for every single actuator as the leak tightness value is always at least just as high as the actual leak rate of this actuator.

Alternatively, however, other mean value formations are also conceivable in which e.g. no averaging over time takes place, but rather the pressure drop per time unit which is determined for the different combinations of actuators, is taken into the end result in the same manner in each case. It is equally conceivable to allow the number of actuators on which pressure is exerted to flow into the averaging.

It is possible by the method in accordance with the invention also to ensure a reliable recognition of leaks for a plurality of actuators during the ongoing operation of the treatment machine. A typical number of actuators e.g. amounts to 16. In accordance with the invention, all 16 valves can thus be monitored via one single pressure gage during the ongoing operation in that the pressure drop values determined during different combinations of switched actuators are respectively associated with the active actuators.

A result vector results in this connection in which the leak tightness value is stored for each individual actuator and is updated in each case on the change from one combination into another combination. An approximation to the actual total situation of the system thus results by the frequent repetition of the measuring method in accordance with the invention with different patterns.

The result vector can then be further processed for the leak recognition. The range of the leak rate can thus e.g. be determined using a minimum/maximum evaluation of the result vector. A narrow range in which all the actuators have similar leak tightness rates is an indicator for a properly operating system. A wide range, in contrast, indicates a possible leak. Furthermore, a change in the leak behavior can be recognized using a sum evaluation of the result vector and its gradient over time. A base leak rate of the system can equally be determined using a minimal value formation.

It is possible by the evaluation to recognize a defective actuator since this actuator causes an increased leak rate for every combination in which pressure is exerted on it. This is then reflected in the increased average value for this actuator. It must be noted here that a trend can only be recognized via the frequency of the individual measurements per component. Measurement imprecision phenomena which occur with fast valve path changes and thus with fast changes of actuator combinations are filtered in this process.

If the system discovers a leak tightness value for an actuator which is evaluated as an indicator for a leak, a test can additionally be carried out to check the result. For this purpose, the operation of the treatment device is interrupted and a test routine is carried out. In this connection, it can either be a known initial test in which all the actuators are checked. Alternatively, initially only the actuator or the group of actuators can also be checked in which the leak was recognized based on the corresponding leak tightness value which was outside a permitted range.

If an actuator has been identified as leaking, the treatment machine can change into a safe state. If, however, sufficient alternatives for the defective actuator are present, the operation can also be continued while bypassing this actuator.

It is thus possible by the method in accordance with the invention to monitor all the actuators with respect to their leak tightness constantly during the ongoing operation of the treatment machine and to react as required.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

TABLE

| | Open −/ Closed + | Current pressure | Current meas. time | Sum pressure drop | Sum measuring time | Evaluation Mbar/min: |
|---|---|---|---|---|---|---|
| Pattern 1 | V1 + | 20 mbar | 1 min | 20 mbar | 1 min | 20 |
| | V2 + | 20 mbar | 1 min | 20 mbar | 1 min | 20 |
| | V3 + | 20 mbar | 1 min | 20 mbar | 1 min | 20 |
| Pattern 2 | V1 + | 25 mbar | 5 min | 45 mbar | 6 min | 7.5 |
| | V2 − | — | — | 20 mbar | 1 min | 20 |
| | V3 − | — | — | 20 mbar | 1 min | 20 |
| Pattern 3 | V1 + | 40 mbar | 2 min | 85 mbar | 8 min | 10.6 |
| | V2 + | 40 mbar | 2 min | 60 mbar | 3 min | 20 |
| | V3 − | — | — | 20 mbar | 1 min | 20 |
| Pattern 4 | V1 − | — | — | 85 mbar | 8 min | 10.6 |
| | V2 + | 15 mbar | 1 min | 75 mbar | 4 min | 18.8 |
| | V3 + | 15 mbar | 1 min | 35 mbar | 2 min | 17.5 |

TABLE-continued

|  |  | Open −/ Closed + | Current pressure | Current meas. time | Sum pressure drop | Sum measuring time | Evaluation Mbar/min: |
|---|---|---|---|---|---|---|---|
| Pattern 5 | V1 | − | — | — | 85 mbar | 8 min | 10.6 |
|  | V2 | − | — | — | 75 mbar | 4 min | 18.8 |
|  | V3 | + | 0 mbar | 5 min | 35 mbar | 7 min | 5 |
| Pattern 6 | V1 | + | 5 mbar | 1 min | 90 mbar | 9 min | 10 |
|  | V2 | − | — | — | 75 mbar | 4 min | 18.8 |
|  | V3 | + | 5 mbar | 1 min | 40 mbar | 8 min | 5 |
| Pattern 7 | V1 | − | — | — | 90 mbar | 9 min | 10 |
|  | V2 | + | 75 mbar | 5 min | 150 mbar | 9 min | 18.8 |
|  | V3 | − | — | — | 40 mbar | 8 min | 5 |

What is claimed is:

1. A method of monitoring leak-tightness of an individual valve actuator and/or an individual group of valve actuators out of a plurality of pneumatically or hydraulically actuated valve actuators of a medical treatment machine, the medical treatment machine including a central pressure supply for the plurality of valve actuators, said method comprising the following steps:
collecting a plurality of pressure drop values associated with a plurality of different sub-groups of the plurality of valve actuators by determining, for each sub-group, a pressure drop value, by performing, for each sub-group, the following sub-steps:
exerting pressure on the sub-group of valve actuators by connecting the sub-group of valve actuators to the central pressure supply, and
measuring a pressure drop value of the central pressure supply associated with the sub-group; and
determining a leak tightness value for the individual valve actuator and/or the individual group of valve actuators based on the following sub-steps:
determining a sub-set of the plurality of pressure drop values, by determining, for each of the plurality of different sub-groups, whether the individual valve actuator or the individual group of value actuators formed part of the sub-group, and, if the individual valve actuator or the individual group of valve actuators formed part of a sub-group, including a pressure drop value associated with the sub-group in the sub-set, and
determining the leak tightness value based on the determined sub-set of pressure drop values.

2. The method in accordance with claim 1, wherein the pressure drop is measured during a stationary operating phase of the associated sub-group of valve actuators.

3. The method in accordance with claim 1, wherein the leak tightness value is additionally based on a measuring time associated with each pressure drop value out of the sub-set of pressure drop values.

4. The method in accordance with claim 3, wherein the leak tightness value is determined on the basis of pressure drop per time unit values each determined from a pressure drop value and an associated measuring time.

5. The method in accordance with claim 3, wherein the measuring time for a pressure drop value is chosen as the duration of a stationary operating phase of the associated sub-group of valve actuators for which the pressure drop is measured.

6. The method in accordance with claim 1, wherein the step of determining the leak tightness value includes determining one out of a mean value over the sub-set of pressure drop values, and a mean value over pressure drop per time unit values associated with the sub-set of pressure drop values.

7. The method in accordance with claim 6, wherein the mean value is a weighted mean value.

8. The method in accordance with claim 7, wherein the step of determining the weighted mean value includes determining a number of value actuators in a sub-group of valve actuators.

9. The method in accordance with claim 6, wherein the step of derminin the mean value includes determining, independently of the number of the valve actuators in a sub-group of valve actuators, a measured pressure drop for each sub-group of valve actuators.

10. The method in accordance with claim 1, wherein the step of determining the leak tightness value includes determining a pressure drop measured for each sub-group of valve actuators on which the pressure is exerted in equal amounts.

11. The method in accordance with claim 1, wherein the step of determining the leak tightness value includes continuously updating the leak tightness values of the individual valve actuators and/or the individual groups of valve actuators during operating of the medical treatment machine.

12. The method in accordance with claim 1, wherein a range of the determined leak tightness values is used for monitoring the valve actuators.

13. The method in accordance with claim 1, wherein a sum of all of the determined leak tightness values is used for monitoring the valve actuators.

14. The method in accordance with claim 1, wherein a change of the determined leak tightness values over time is used for monitoring the valve actuators.

15. The method in accordance with claim 1, wherein, upon a recognition of a leak, operation of the medical treatment machine is stopped and a test is carried out.

16. The method in accordance with claim 15, wherein a test is carried out in which the individual valve actuators and/or the individual groups of valve actuators in which a leak was recognized is checked.

17. The method in accordance with claim 1, wherein an initial test is carried out in which all of the valve actuators are checked.

18. The method in accordance with claim. 1, wherein upon at least one of a recognition and a confirmation of a leak, the valve actuator that is leaking is no longer used or the medical treatment machine changes into a safe state.

19. The method in accordance with claim 1, wherein the method controls the valve actuators associated with valves of a cassette for the transport of a medical liquid.

20. The method in accordance with claim 1, wherein said steps of collecting and determining are effected while said medical treatment machine is in communication with a patient to whom said medical treatment is being provided.

21. A medical treatment machine comprising:
a plurality of pneumatically or hydraulically actuatable valve actuators, a central pressure supply that provides the plurality of valve actuators with pressure, a pressure gauge for measurement of the pressure of the central pressure supply, and an electronic control which controls the valve actuators by connecting the valve actuators to the central pressure supply,
with the electronic control collecting a plurality of pressure drop values associated with a plurality of different sub-groups of the plurality of valve actuators by determining, for each sub-group, a pressure drop value, by performing, for each sub-group, the following sub-steps:
  exerting pressure on the sub-group of valve actuators by connecting the sub-group of valve actuators to the central pressure supply, and
  measuring a pressure drop value of the central pressure supply associated with the sub-group;
an elevation unit that determines a leak tightness value for an individual valve actuator and/or an individual group of valve actuators by performing the following sub-steps:
determining a sub set of the plurality of pressure drop values, by determining, for each of the plurality of different sub-groups, whether the individual valve actuators or the individual group of valve actuators formed part of the sub-group, and, if the individual valve actuator or the individual group of valve actuators formed part of a sub-group, including a pressure drop value associated with the sub-group in the sub-set, and
determining the leak tightness value based on the determined sub-set of pressure drop values; and
a monitoring unit that monitors the leak tightness of the valve actuators based on the determined leak tightness values.

22. The medical treatment machine in accordance with claim 21, wherein the electronic control collects a measuring time associated with each pressure drop value.

23. The medical treatment machine in accordance with claim 21, wherein the electronic control measures a pressure drop value associated with a sub-group of valve actuators for a duration of a stationary operating phase of the associated sub-group of valve actuators.

24. The medical treatment machine in accordance with claim 21, wherein, for determining a leak tightness value, the medical treatment machine determines a pressure drop per time unit value calculated from a measured pressure drop value and an associated measuring time.

25. The medical treatment machine in accordance with claim 21, wherein the evaluation unit determines one out of a mean value over the sub-set of pressure drop values and a mean value over pressure drop per time unit values associated with the sub-set of pressure drop values.

26. The medical treatment machine in accordance with claim 25, wherein the mean value is a weighted mean value.

27. The medical treatment machine in accordance with claim 26, wherein for determining the weighted mean value, the evaluation unit determines a number of value actuators in a sub-group of valve actuators.

28. The medical treatment machine in accordance with claim 25, wherein for determining the mean value, the evaluation unit determines, independently of the number of the valve actuators in a sub-group of valve actuators, a measured pressure drop for each sub-group of valve actuators.

29. The medical treatment machine in accordance with claim 21, wherein the evaluation unit determines a sum of all pressure drop values in the sub-set of pressure drop values and a sum of associated measuring times.

30. The medical treatment machine in accordance with claim 21, wherein the evaluation unit continuously updates the leak tightness values of the individual valve actuators and/or the individual groups of valve actuators during operation of the medical treatment machine.

31. The medical treatment machine in accordance with claim 21, wherein the monitoring unit monitors the leak tightness of the valve actuators based on a range of the determined leak tightness values.

32. The medical treatment machine in accordance with claim 21, wherein the monitoring unit monitors the leak tightness of the valve actuators based on a sum of all of the determined leak tightness values.

33. The medical treatment machine in accordance with claim 21, wherein the monitoring unit monitors the leak tightness of the valve actuators based on a change over time of the determined leak tightness values.

34. The medical treatment machine in accordance with claim 21, wherein, upon a recognition of a leak, the monitoring unit stops operation of the medical treatment machine, and carries out a test.

35. The medical treatment machine in accordance with claim 34, wherein the monitoring unit carries out a test in which the individual valve actuators and/or the individual groups of valve actuators for which a leak was recognized is checked.

36. The medical treatment machine in accordance with claim 21, wherein the monitoring unit carries out an initial test in which all of the valve actuators are checked.

37. The medical treatment machine in accordance with claim 21, wherein the electronic control, upon at least one of a recognition and a confirmation of a leak, no longer uses the valve actuator that is leaking, or switches the medical treatment machine into a safe state.

38. The medical treatment machine in accordance with claim 21, wherein the valve actuators are associated with valves of a cassette for the transport of a medical liquid.

39. The medical treatment in accordance with claim 38, further comprising a coupling surface to which a cassette is coupleable for the transport of a medical liquid, with the valve actuators being arranged at the coupling surface.

40. The medical treatment machine according to claim 21, further comprising a non-transitory computer readable medium for the monitoring of the leak tightness of the valve actuators.

41. The medical treatment machine in accordance with claim 21, wherein the medical treatment machine is for dialysis.

42. The medical treatment machine in accordance with claim 21, said medical treatment machine being configured such that the exerting of the pressure, the measuring of the pressure drop values, and the determining of the leak tightness value are performed while a medical treatment is being effected with the medical treatment machine.

* * * * *